(12) United States Patent
Ruan et al.

(10) Patent No.: US 9,562,113 B2
(45) Date of Patent: *Feb. 7, 2017

(54) LABELED ALGINATE CONJUGATES FOR MOLECULAR IMAGING APPLICATIONS

(71) Applicant: Bellerophon BCM LLC, Hampton, NJ (US)

(72) Inventors: Fuqiang Ruan, Bellevue, WA (US); Thomas L. Deckwerth, Seattle, WA (US); Martin D. Meglasson, Bloomsbury, NJ (US)

(73) Assignee: Bellerophon BCM LLC, Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/989,041

(22) Filed: Jan. 6, 2016

(65) Prior Publication Data

US 2016/0115252 A1    Apr. 28, 2016

Related U.S. Application Data

(60) Continuation of application No. 14/602,504, filed on Jan. 22, 2015, now Pat. No. 9,260,399, which is a division of application No. 13/708,306, filed on Dec. 7, 2012, now Pat. No. 8,974,766.

(60) Provisional application No. 61/568,796, filed on Dec. 9, 2011.

(51) Int. Cl.
| | |
|---|---|
| *A61K 51/00* | (2006.01) |
| *A61M 36/14* | (2006.01) |
| *C08B 37/00* | (2006.01) |
| *A61K 51/06* | (2006.01) |
| *C07B 59/00* | (2006.01) |
| *C07D 255/02* | (2006.01) |
| *C07F 1/08* | (2006.01) |
| *C07F 5/00* | (2006.01) |
| *A61K 49/04* | (2006.01) |
| *A61K 51/04* | (2006.01) |

(52) U.S. Cl.
CPC .......... *C08B 37/0084* (2013.01); *A61K 49/04* (2013.01); *A61K 51/065* (2013.01); *C07B 59/002* (2013.01); *C07D 255/02* (2013.01); *C07F 1/08* (2013.01); *C07F 5/003* (2013.01); *A61K 51/04* (2013.01)

(58) Field of Classification Search
USPC ........................................................ 424/1.73
See application file for complete search history.

(56) References Cited

U.S. PATENT DOCUMENTS

| | | | |
|---|---|---|---|
| 5,834,020 A | 11/1998 | Margerum et al. | |
| 8,974,766 B2 * | 3/2015 | Ruan | A61K 51/065 424/1.73 |
| 9,260,399 B2 * | 2/2016 | Ruan | A61K 51/065 |
| 2008/0107606 A1 | 5/2008 | Grotjahn | |
| 2012/0009124 A1 | 1/2012 | Port et al. | |

FOREIGN PATENT DOCUMENTS

WO    WO 2010/066051    6/2010

OTHER PUBLICATIONS

PCT International Search Report and Written Opinion in PCT/US2012/068546, mailed Jan. 25, 2013, 11 pages.
PCT International Preliminary Report on Patentability in PCT/US2012/068546, dated Jun. 10, 2014, 5 pages.
Non-Final Office Action in U.S. Appl. No. 13/708,306, dated Mar. 17, 2014, 6 pages.
Gruwel, Marco L., et al., Magnetic resonance imaging tracking of alginate beads used for drug delivery of growth factors at sites of cardiac damage, *Magnetic Resonance Imaging 27* 2009, 970-975.
Mourino, V., et al., Physicochemical, biological and drug-release properties of gallium crosslinked alginate/nanoparticulate bioactive glass composite films, *Soft Matter No. 7* 2011, 6705-6712.
Mourino, Vivana, et al., Preparation and Characterization of Gallium Releasing 3-D Alginate Coated 45S5 Bioglass Based Scaffolds for Bone Tissue Engineering, *Advanced Engineering Materials*, 12 No. 7 2010 B283-B291.
Wadas, Thaddeus, J., et al., Coordinating Radiometals of Copper, Gallium, Indium, Yttrium, and Zirconium for PET and SPECT Imaging of Disease, *Chem. Rev. vol. 110 No. 5* ,2858-2902.

* cited by examiner

*Primary Examiner* — Frederick Krass
*Assistant Examiner* — Melissa Perreira
(74) *Attorney, Agent, or Firm* — Servilla Whitney LLC

(57) ABSTRACT

Described are bifunctional NOTA-based derivatives capable of conjugating with alginate and with metal ions, as well as NOTA-alginate conjugates which can be labeled with stable or radioactive metal ions. Also described are conjugation methods of the bifunctional NOTA-based linker with alginate, and methods of using radiometal-labeled NOTA-alginate conjugates or other radio-labeled alginate conjugates as imaging reagents.

14 Claims, No Drawings

LABELED ALGINATE CONJUGATES FOR MOLECULAR IMAGING APPLICATIONS

CROSS-REFERENCE TO RELATED APPLICATIONS

This application is a continuation of U.S. patent application Ser. No. 14/602,504, filed Jan. 22, 2015, which is a divisional of U.S. patent application Ser. No. 13/708,306, filed Dec. 7, 2012, issued as U.S. Pat. No. 8,974,766, which claims the benefit under 35 U.S.C. §119(e) of U.S. Provisional Application No. 61/568,796, filed Dec. 9, 2011, the entire contents of which are incorporated herein by reference in their entireties.

TECHNICAL FIELD

The present invention generally relates to the field of alginate conjugates and their use as imaging reagents.

BACKGROUND

Cross-linked polymer hydrogel materials are widely utilized in the biomedical industry. They are used in contact lenses, blood contact materials, controlled release formulations, wound dressings, bioadhesives, membranes, superabsorbents, cell encapsulation and immunoisolation materials, and tissue engineering scaffolds. Among the different polymers, the naturally occurring polysaccharide alginic acid has found biomedical applications because of its biocompatibility, relative biological inertness, and the ability to engineer its mechanical properties by introducing various types of chemical and physical crosslinks. Alginic acid distinguishes itself from other biologically occurring polysaccharides in its ability to form stiff hydrogels when exposed to cross-linking calcium ions at slightly supraphysiological concentrations. This property has been utilized to devise a treatment for damaged heart tissue of patients at risk for adverse remodeling of the left ventricle of the heart following acute myocardial infarction (AMI). An aqueous soluble formulation of sodium alginate and calcium-D-gluconate, the concentration of each component carefully chosen to achieve partial crosslinking of the alginate molecules, yet providing for a stable free flowing liquid, is injected into the coronary artery of AMI patients after revascularization. The formulation undergoes a transition from liquid to gel when in contact with the infarcted cardiac tissue as a result of the elevated extracellular calcium concentration in the re-perfused cardiac tissue. The hydrogel then deposits in the interstitial tissue and exerts a beneficial therapeutic effect by reducing adverse remodeling and heart failure, potentially because of its mechanical support of the weakened heart wall.

The deposition of this alginate hydrogel in the injured reperfused myocardium of AMI patients is unknown as comprehensive invasive heart tissue sampling in human patients cannot be conducted. Also, the utility of invasive tissue sampling techniques in a preclinical setting is limited because the surgical intervention often constitutes a terminal procedure that prevents longitudinal assessment in the same research subject. Non-invasive imaging techniques can offer a solution by providing this information without surgical intervention or terminal procedures. Imaging modalities such as echocardiography, computed tomography, magnetic resonance imaging, and nuclear imaging such as positron emission tomography (PET) and single photon emission computed tomography (SPECT) use specialized imaging reagents and/or instrumentation to assess heart structure, function, perfusion and remodeling in patients with AMI or heart failure as well as in animal models of these diseases.

SUMMARY

One aspect of the present invention relates to a compound having the formula:

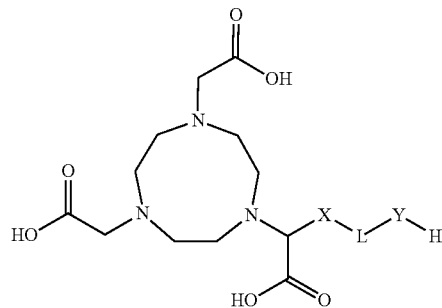

wherein X is —$(CH_2)_m C(O)$—, with m being 1, 2, or 3;
L is a linker selected from the group consisting of:

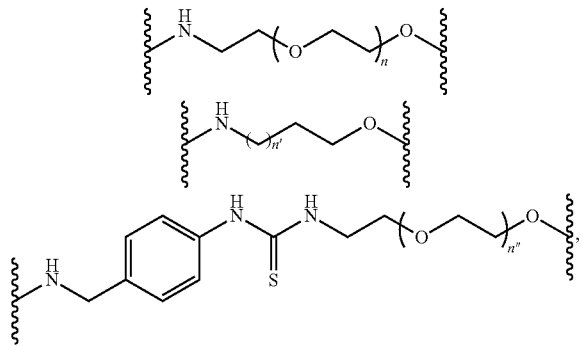

wherein n, n' and n" are each independently a number from 0 to 10; and
Y—H is selected from the group consisting of:

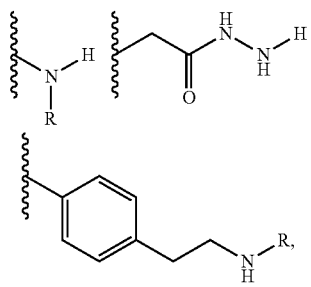

wherein R is selected from the group consisting of hydrogen, alkyl, benzyl or an aromatic group;
or a pharmaceutically acceptable salt or solvate thereof.

In certain embodiments of this aspect, the compound further comprises a stable or radioactive metal ion chelated by the 1,4,7-triazacyclononane-1,4,7-triacetic acid moiety. According to one or more embodiments, the stable or radioactive metal ion comprises a gallium ion. In some embodiments, the gallium ion is one suitable for imaging, such as $^{66}$Ga, $^{67}$Ga or $^{68}$Ga. In other embodiments, the radioactive metal ion is one suitable for imaging, such as $^{60}$Cu, $^{61}$Cu, $^{62}$Cu, $^{64}$Cu, $^{67}$Cu, or $^{111}$In.

Another aspect of the invention pertains to an alginate conjugate having the formula:

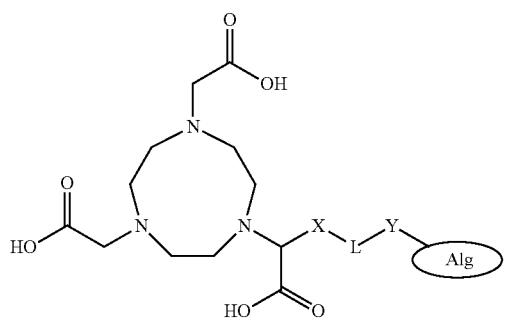

wherein X is —(CH$_2$)$_m$C(O)—, with m being 1, 2, or 3;
L is a linker selected from the group consisting of:

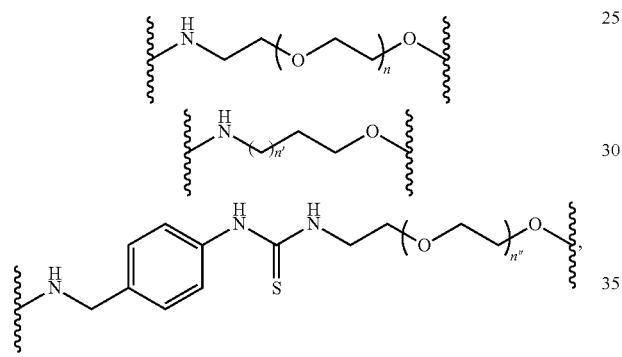

wherein n, n' and n" are each independently a number from 0 to 10;
Alg is alginic acid or an alginate salt; and
Y is a spacer directly attached to the reducing end unit of alginate or the carboxyl groups of the alginate polymer chain via the active nitrogen, and selected from the group consisting of:

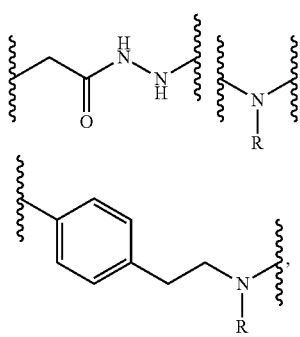

wherein R is selected from the group consisting of hydrogen, alkyl, benzyl or an aromatic group;
or a pharmaceutically acceptable salt or solvate thereof.
In one or more embodiments, the alginate salt comprises a monovalent cation salt and/or a multivalent cation salt. The monovalent and/or multivalent cation may comprise one or more of sodium, potassium, lithium, rubidium, cesium, ammonium, calcium, strontium, barium and magnesium. In some embodiments, the alginate salt is sodium alginate, calcium alginate, or a mixture of sodium alginate and calcium alginate.

According to one or more embodiments of this aspect, the conjugate further comprises a stable or radioactive metal ion chelated by the 1,4,7-triazacyclononane-1,4,7-triacetic acid moiety of the conjugate. In certain embodiments, the stable or radioactive metal ion comprises gallium ion. Some embodiments provide that the gallium ion is one suitable for imaging, such as $^{66}$Ga, $^{67}$Ga or $^{68}$Ga. In other embodiments, the radioactive metal ion comprises one suitable for imaging such as $^{60}$Cu, $^{61}$Cu, $^{62}$Cu, $^{64}$Cu, $^{67}$Cu, or $^{111}$In.

In one or more embodiments, the stable or radioactive metal ion is chelated by the 1,4,7-triazacyclononane-1,4,7-triacetic acid moiety of the conjugate at a temperature between 20° C. to 100° C.

Another aspect of the invention relates to a method of imaging in a mammal comprising administering a radio-labeled alginate conjugate to a mammal, and imaging the temporal and spatial distribution of the radio-labeled alginate conjugate. According to one or more embodiments of this aspect, the alginate conjugate has the formula:

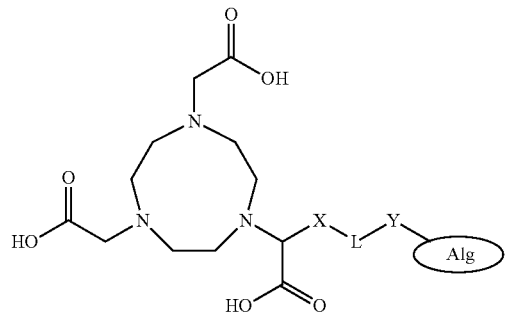

wherein X is —(CH$_2$)$_m$C(O)—, with m being 1, 2, or 3;
L is a linker selected from the group consisting of:

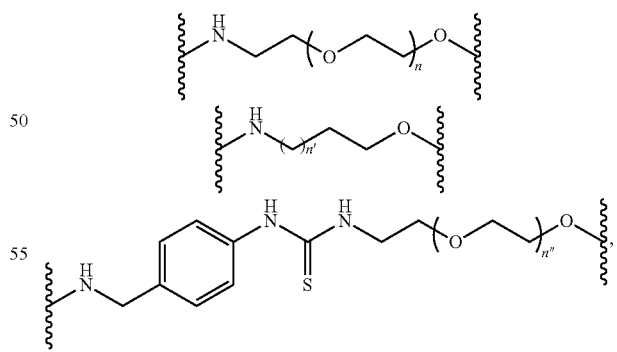

wherein n, n' and n" are each independently a number from 0 to 10;
Alg is alginic acid or an alginate salt; and
Y is a spacer directly attached to the reducing end unit of alginate or the carboxyl groups of the alginate polymer chain via the active nitrogen, and selected from the group consisting of:

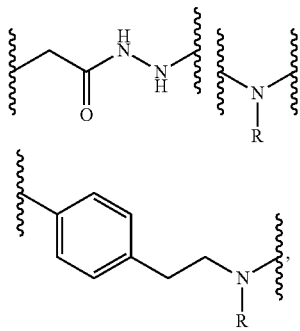

wherein R is selected from the group consisting of hydrogen, alkyl, benzyl or an aromatic group;

or a pharmaceutically acceptable salt or solvate thereof, and the alginate conjugate further comprises a stable or radioactive metal ion chelated by the 1,4,7-triazacyclononane-1,4,7-triacetic acid moiety of the conjugate.

In one or more embodiments, the alginate salt comprises a monovalent cation salt and/or a multivalent cation salt. The monovalent and/or multivalent cation may comprise one or more of sodium, potassium, lithium, rubidium, cesium, ammonium, calcium, strontium, barium and magnesium. In some embodiments, the alginate salt is sodium alginate, calcium alginate, or a mixture of sodium alginate and calcium alginate.

In certain embodiments, the stable or radioactive metal ion comprises a gallium ion. Some embodiments provide that the gallium ion is one suitable for imaging, such as $^{66}Ga$, $^{67}Ga$ or $^{68}Ga$. In other embodiments, the radioactive metal ion comprises one suitable for imaging such as $^{60}Cu$, $^{61}Cu$, $^{62}Cu$, $^{64}Cu$, $^{67}Cu$, or $^{111}In$.

In other embodiments, the alginate is conjugated to an iodinated tyramine or tyramine derivative. In some embodiments, the iodinate tyramine or tyramine derivative may have the following formula:

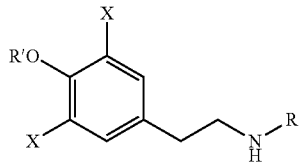

wherein each X is independently hydrogen or iodine and R and R' are each independently hydrogen, alkyl, benzyl or an aromatic group. In some embodiments, the iodine is selected from the isotopes of $^{123}I$, $^{124}I$, $^{125}I$ and $^{131}I$.

In some embodiments of this method, the mammal is a human.

Another aspect of the invention relates to a method of imaging alginate deposition in a mammal comprising administering a radio-labeled alginate conjugate to a mammal and imaging the radio-labeled alginate conjugate. In certain embodiments, the radio-labeled alginate conjugate is partially cross-linked.

According to one or more embodiments of this aspect, the alginate conjugate has the formula:

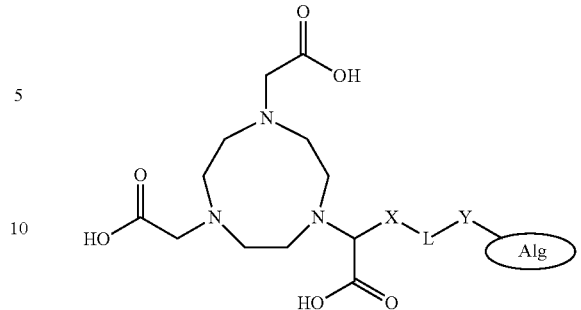

wherein X is —$(CH_2)_mC(O)$—, with m being 1, 2, or 3;
L is a linker selected from the group consisting of:

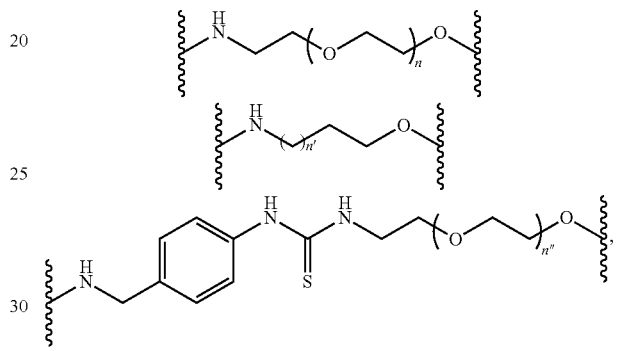

wherein n, n' and n'' are each independently a number from 0 to 10;
Alg is alginic acid or an alginate salt; and
Y is a spacer directly attached to the reducing end unit of alginate or the carboxyl groups of the alginate polymer chain via the active nitrogen, and selected from the group consisting of:

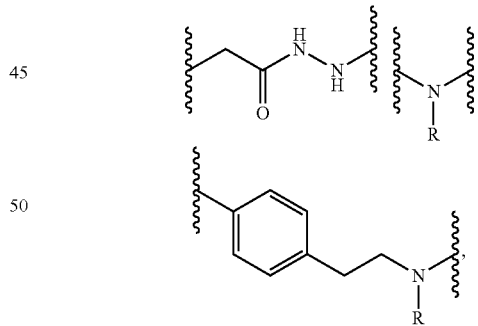

wherein R is selected from the group consisting of hydrogen, alkyl, benzyl or an aromatic group;

or a pharmaceutically acceptable salt or solvate thereof, and the alginate conjugate further comprises a stable or radioactive metal ion chelated by the 1,4,7-triazacyclononane-1,4,7-triacetic acid moiety of the conjugate.

In one or more embodiments, the alginate salt comprises a monovalent cation salt and/or a multivalent cation salt. The monovalent and/or multivalent cation may comprise one or more of sodium, potassium, lithium, rubidium, cesium, ammonium, calcium, strontium, barium and magnesium. In some embodiments, the alginate salt is sodium alginate, calcium alginate, or a mixture of sodium alginate and calcium alginate.

In certain embodiments, the stable or radioactive metal ion comprises a gallium ion. Some embodiments provide that the gallium ion is one suitable for imaging, such as $^{66}$Ga, $^{67}$Ga or $^{68}$Ga. In other embodiments, the radioactive metal ion comprises one suitable for imaging such as $^{60}$Cu, $^{61}$Cu, $^{62}$Cu, $^{64}$Cu, $^{67}$Cu, or $^{111}$In.

In other embodiments, the alginate is conjugated to an iodinated tyramine or tyramine derivative. In some embodiments, the iodinate tyramine or tyramine derivative may have the following formula:

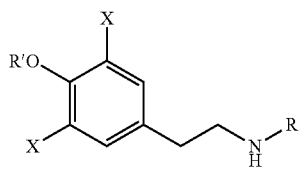

wherein each X is independently hydrogen or iodine and R and R' are each independently hydrogen, alkyl, benzyl or an aromatic group. In some embodiments, the iodine is selected from the isotopes of $^{123}$I, $^{124}$I, $^{125}$I and $^{131}$I.

In some embodiments of this method, the mammal is a human.

Yet another aspect of the invention relates to a method of imaging alginate deposition in a mammal comprising administering a radio-labeled alginate conjugate and partially calcium-cross-linked alginate to a mammal and imaging the radio-labeled alginate conjugate. In certain embodiments, the radio-labeled alginate conjugate is partially cross-linked.

According to one or more embodiments of this aspect, the alginate conjugate has the formula:

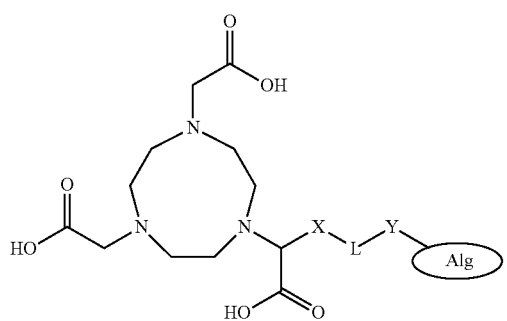

wherein X is —(CH$_2$)$_m$C(O)—, with m being 1, 2, or 3;
L is a linker selected from the group consisting of:

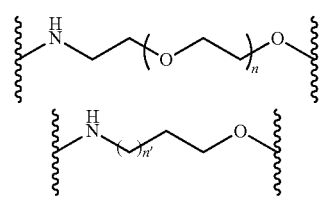

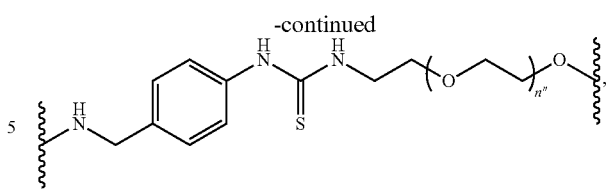

wherein n, n' and n" are each independently a number from 0 to 10;
Alg is alginic acid or an alginate salt; and
Y is a spacer directly attached to the reducing end unit of alginate or the carboxyl groups of the alginate polymer chain via the active nitrogen, and selected from the group consisting of:

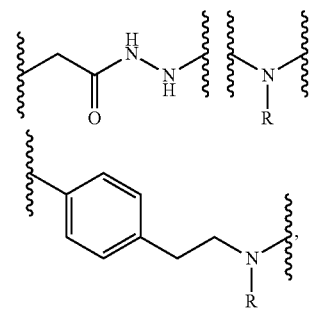

wherein R is selected from the group consisting of hydrogen, alkyl, benzyl or an aromatic group;
or a pharmaceutically acceptable salt or solvate thereof, and the alginate conjugate further comprises a stable or radioactive metal ion chelated by the 1,4,7-triazacyclononane-1,4,7-triacetic acid moiety of the conjugate.

In one or more embodiments, the alginate salt comprises a monovalent cation salt and/or a multivalent cation salt. The monovalent and/or multivalent cation may comprise one or more of sodium, potassium, lithium, rubidium, cesium, ammonium, calcium, strontium, barium and magnesium. In some embodiments, the alginate salt is sodium alginate, calcium alginate, or a mixture of sodium alginate and calcium alginate.

In certain embodiments, the stable or radioactive metal ion comprises a gallium ion. Some embodiments provide that the gallium ion is one suitable for imaging, such as $^{66}$Ga, $^{67}$Ga or $^{68}$Ga. In other embodiments, the radioactive metal ion comprises one suitable for imaging such as $^{60}$Cu, $^{61}$Cu, $^{62}$Cu, $^{64}$Cu, $^{67}$Cu, or $^{111}$In.

In other embodiments, the alginate is conjugated to an iodinated tyramine or tyramine derivative. In some embodiments, the iodinate tyramine or tyramine derivative may have the following formula:

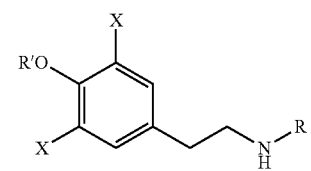

wherein each X is independently hydrogen or iodine and R and R' are each independently hydrogen, alkyl, benzyl or an aromatic group. In some embodiments, the iodine is selected from the isotopes of $^{123}$I, $^{124}$I, $^{125}$I and $^{131}$I.

In some embodiments of this method, the mammal is a human.

The foregoing has outlined rather broadly certain features and technical advantages of the present invention. It should be appreciated by those skilled in the art that the specific embodiments disclosed may be readily utilized as a basis for modifying or designing other structures or processes within the scope present invention. It should also be realized by those skilled in the art that such equivalent constructions do not depart from the spirit and scope of the invention as set forth in the appended claims.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Embodiments of the current invention provide for novel nuclear imaging reagents based on alginate conjugates for non-invasive clinical and preclinical imaging of the heart and other organs and tissues. Such imaging reagents are useful in measuring the kinetics of alginate deposition in the injured myocardium and other bodily organs and tissues, and also may be useful to identify tissues or organs with supra-physiological calcium concentration.

Sodium alginate is the structural polysaccharide that provides marine seaweed with its flexibility and strength. It is a linear binary block copolymer consisting of (1→4)-linked β-D-mannuronic and α-L-guluronic acid residues in various ratios and sequence arrangements. Calcium binding is mediated by rigid homopolymeric guluronate sequences (G-blocks); the mannuronate blocks (M-blocks) do not bind calcium but provide for flexible linkers connecting the calcium-binding G-blocks. According to the egg box model of calcium binding, one calcium ion is bound by two guluronate dimers located on two nearby alginate molecules, each dimer formed by two adjacent guluronate residues. Calcium binding by G-blocks on alginate molecules is cooperative, leading to the formation of a zipper-like structure that crosslinks different alginate molecules in a three-dimensional network. The crosslinking of alginate molecules with calcium ions in aqueous solution induces the formation of a mechanically resilient hydrogel that can be disassembled by removal or chelation of calcium.

To follow alginate hydrogel formation and deposition in mammals after intracoronary injection, a labeling strategy for alginate was developed that allows the imaging of alginate hydrogel formation and deposition by PET or SPECT. A radiometal approach was chosen over other radioligand methodologies since (1) an unlabeled alginate conjugate precursor can be prepared in advance of the radioactive labeling; (2) the gelling properties of the conjugate can be adjusted by choosing the extent and type of substitution to mimic those of native alginate; (3) a properly designed conjugate can be labeled with a radioactive metal ion in a fast and mild binding reaction that is chemically compatible with alginate; (4) the radiometal-labeled conjugate can be quickly and quantitatively separated from free unbound radiometal; (5) the time required to prepare the radiometal-labeled alginate is short relative to the half-life of the radiometal. However, in some embodiments, the alginate is radiolabeled with other possible radioligands, such as iodinated tyramine or tyramine derivatives.

In addition to the physiological crosslinking agent calcium, many other di- and trivalent cations of transition and heavy metals may bind alginate. Examples of such metals include Mg, Sr, Ba, Mn, Cu, Zn, Co, Cr, Al, Fe, Ga, In, Re, Pb, Hg and U. The direct metal binding by alginate has found many applications ranging from the removal of toxic and radioactive metal contaminants from drinking and waste water to imaging applications with the radiometal $^{111}$In or imaging/radiotherapy applications for $^{188}$Re. The direct binding of a radiometal to alginate has a number of disadvantages, however. For example, pathologically elevated tissue calcium may compete with the radiometal for alginate binding and may induce the release of the metal ion from the alginate polymer, this rendering the radiometal useless for tracking alginate deposition. Also, the binding of the radiometal to the calcium binding sites may alter the gelation properties of alginate which is undesirable for an imaging reagent that is meant to mimic the deposition of alginate in a myocardial infarct.

Ligation of the radiometal to the alginate polymer via a bifunctional linker molecule has potential several advantages over binding of the radiometal to the calcium binding sites of alginate: (1) the binding of the radiometal to a suitably engineered bifunctional linker can be engineered to be of high affinity while the affinity of direct metal binding to the alginate polymer is low and is given by the structure of alginate; (2) binding of calcium to alginate to induce gelation does not compete for radiometal binding to the alginate conjugate, since calcium has only low affinity for a properly designed bifunctional linker; (3) the radioactive concentration of the radiometal-labeled alginate can be controlled by the ratio of chelator attached to alginate; and (4) the binding of multivalent metals to alginate via a bifunctional chelator does not cause hydrogel formation by crosslinking of alginate molecules.

Sodium alginate can be chemically modified by attaching chemical moieties to the polymer. Examples include derivatization with bifunctional crosslinking agents to covalently crosslink alginate chains into a three-dimensional hydrogel that is independent of the calcium concentration. Monofunctional reagents have been covalently bound to attach radioactive or histochemical labels that allow measuring alginate deposition and degradation. Such chemical moieties can be attached to reactive groups present on the alginate polymer. Each hexuronic acid residue of the alginate polymer has one carboxyl group and two hydroxyl groups that can be chemically modified. Moreover, each entire sodium alginate molecule has one single reducing end to which one molecule can be conjugated. In addition, reactive aldehydes can be generated along the polymer by gentle oxidation of the C2-C3 carbon-carbon bond. Derivatization chemistries for stable modification of alginate on these sites include amide bond formation via activated ester, Schiff-base formation and reductive amination, among others.

Many different types of metal chelators have been developed to bind radiometals to biological molecules. Examples of such chelators can be found in the review by Wadas et al. 2010 (Chem. Rev. 110: 2858-2902), which is hereby incorporated by reference in its entirety. The chelators differ in their chemical structure and their affinity and binding kinetics for different metal ions and have different optimum binding conditions required for metal complex formation. Many commonly used chelators with high stability of the metal-chelator complex in vivo require elevated temperature, e.g. 100° C., for efficient metal complex formation.

Such elevated temperatures can be undesirable as they may damage the macromolecule, leading to its degradation or denaturation. As the glycosidic bond of alginate may undergo hydrolysis at elevated temperatures, a chelator is preferred that avoids using high temperatures for complex formation. The formed metal ion-chelator complexes vary in their stability in biological fluids. Biological metal chelators in plasma such as albumin and transferrin may bind free radiometals and will facilitate the disintegration of the metal-chelator complex Several different radiometals used in nuclear imaging can be used to labeling alginate via a suitable metal chelator linked to alginate. In some embodiments, the radiometal is gallium ion. Among the different radiometals, gallium as trivalent $Ga^{III}$ cation may be favored in some embodiments because (1) a single conjugate can be prepared for use with both imaging modalities, PET and SPECT imaging, modalities with sufficient sensitivity, spatial and temporal resolution as gallium isotopes suitable for both imaging modalities exist; (2) the macrocyclic gallium ion chelator 1,4,7-triazacyclononane-1,4,7-triacetic acid (NOTA) forms a high affinity $Ga^{III}$-NOTA complex with gallium within minutes at physiological temperatures (20° C. to 37° C.); this complex is stable in blood; (3) the affinity of NOTA for gallium ion is high enough to avoid significant gallium binding to the calcium binding sites on the alginate polymer during the labeling reaction; and (4) the chelator NOTA can be chemically modified with a spacer molecule to form a bifunctional linker that attaches NOTA to one of the reactive sites of alginate without significantly altering the chelator's binding affinity for gallium ion. However, other suitable radiometals or radioligands as described herein may also be used for radiolabeling the alginate.

Published studies document the binding of gallium to an alginate bioglass biomaterial with the purpose of providing for an antibacterial yet tissue-compatible biomaterial conducive for bone regeneration. This material differs from the gallium-NOTA alginate conjugate described here in that it does not employ a bifunctional linker to enable stable and high-affinity binding of gallium to the alginate polymer but utilizes the weak and reversible binding of gallium ion to the alginate polymer to create a gallium ion-releasing antibacterial scaffold for bone tissue engineering.

Thus the labeling of alginate with gallium metal ion via a bifunctional linker that binds gallium ion and attaches covalently to alginate, the chemical synthesis of a NOTA-containing alginate conjugate, the preparation of a gallium NOTA alginate conjugate and the use of such a gallium-labeled NOTA-alginate conjugate in preclinical and clinical imaging applications are novel and have not been previously reported.

Although specific reference is made to sodium alginate, other alginates are compatible with embodiments of all the aspects described herein. Alginates from different algae and bacterial strains vary in their molecular weight, polydispersity, guluronic acid content, sequence arrangement of G-blocks, M-blocks and GM-blocks, and chemical modification. These differences do not alter their suitability for the described imaging application. Alginates can be fractionated by molecular weight and chemical composition, chemically derivatized or functionalized with cross-linkers or other reagents and prepared in different salt forms including the free acid, neither of which would render the described imaging strategy impossible to pursue.

According to one aspect of the present invention, provided are bifunctional linkers derived from the structure of NOTA having the general structure of Formula (I):

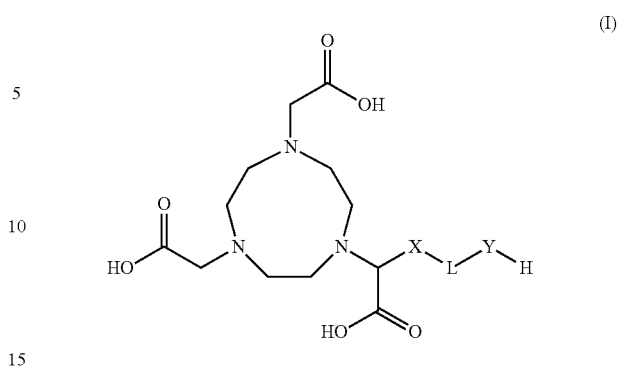

wherein X is —(CH$_2$)—C(O)—; m is 1, 2, or 3; L is a linker; H is hydrogen; and Y—H is a functional group capable of conjugating with alginate via direct attachment or reductive amination to the reducing end, or via amide bond formation with the carboxyl groups on the chain of alginate. In one or more embodiments, the compound is a pharmaceutically acceptable salt or solvate of the compound of Formula (I).

These NOTA-derived linkers are bifunctional molecules that after their conjugation to alginate allow for the labeling of alginate with metal ions. The metal ions can be stable or undergo radioactive decay. In some embodiments, the NOTA-derived linker is labeled with a radioactive metal ion. In some embodiments, the NOTA-derived linker is labeled with $^{66}$Ga, $^{67}$Ga or $^{68}$Ga. In a particular embodiment, the radioactive metal ion is the gamma-ray emitting $^{67}$Ga isotope. In other embodiments, the radioactive metal ion is a positron-emitting $^{66}$Ga or $^{68}$Ga isotope.

In one or more embodiments, linker L has one of the following structures:

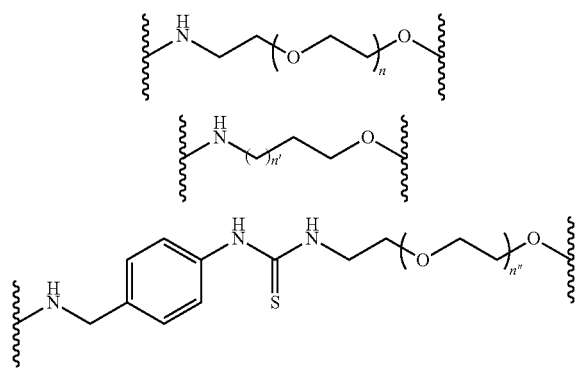

wherein n, n' and n" are each independently a number from 0 to 10.

According to one or more embodiments, Y—H is selected from the group consisting of:

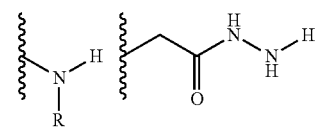

-continued

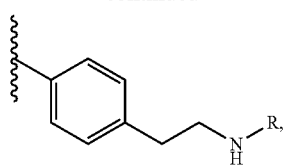

wherein R is selected from the group consisting of hydrogen, alkyl, benzyl or an aromatic group.

Another aspect of the invention relates to a metal-chelator-containing alginate conjugate. In one exemplary embodiment, this conjugate is a NOTA-alginate conjugate having the general structure of Formula (II):

(II)

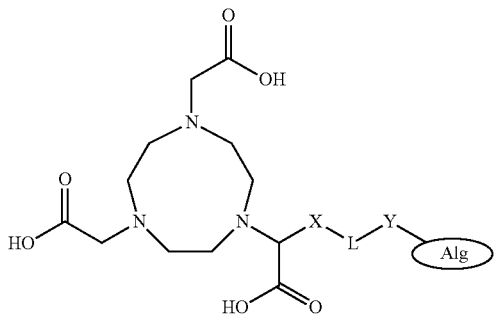

wherein X is —($CH_2$)$_m$—C(O)—; m is 1, 2, or 3; L is a linker; Alg is alginic acid or an alginate salt, Y is a spacer directly attached by reductive amination to the reducing end, or via amide bond formation to the carboxyl groups of the alginate polymer. The molar ratio of NOTA-linker to alginate can be controlled by the conjugation reaction conditions to suit particular needs of the imaging application. In one or more embodiments, the compound is a pharmaceutically acceptable salt or solvate of the compound of Formula (II).

These NOTA-alginate conjugates can be labeled with metal ions. In some embodiments, the NOTA-alginate conjugate is labeled with a radioactive metal ion. In further embodiments, the NOTA-alginate conjugate is labeled with gallium isotopes suitable for imaging applications such as $^{66}$Ga, $^{67}$Ga or $^{68}$Ga. In a preferred embodiment, the radioactive metal ion is the gamma-emitting isotope $^{67}$Ga. In an alternate embodiment, the radioactive metal ion is the positron-emitting $^{66}$Ga or $^{68}$Ga isotope.

In one or more embodiments, L has one of the following structures:

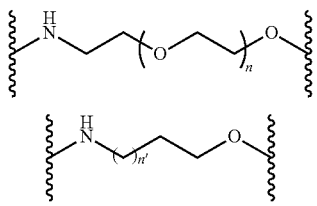

-continued

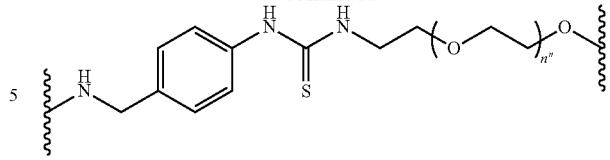

wherein n, n' and n" are each independently a number from 0 to 10.

In one or more embodiments, the alginate salt comprises a monovalent cation salt and/or a multivalent cation salt. The monovalent and/or multivalent cation may comprise one or more of sodium, potassium, lithium, rubidium, cesium, ammonium, calcium, strontium, barium and magnesium. In some embodiments, the alginate salt is sodium alginate, calcium alginate, or a mixture of sodium alginate and calcium alginate.

In certain embodiments, the alginate has a molecular weight between about 10 and about 100 kDa. In a specific embodiment, the alginate has a molecular weight of about 30 kDa.

According to one or more embodiments, Y has one of the following structures:

wherein R is selected from the group consisting of hydrogen, alkyl, benzyl or an aromatic group.

Another aspect of the invention pertains to the use of these conjugates in clinical imaging. Examples of such imaging modalities include, but are not limited to PET or SPECT. Other types of imaging can be used with these radiometal-labeled alginate conjugates. For example, radiometal-labeled alginate conjugates can be employed in imaging by whole-body autoradiography in preclinical settings or with a gamma camera (Anger camera) in clinical or preclinical settings. Such imaging can provide non-invasive monitoring of aqueous cross-linked alginate solution in the bodies of mammals, as well as the visualization of its cardiac deposition. In one or more embodiments, the mammal is a human.

The NOTA-linker or the NOTA-alginate conjugates can be labeled with metal ions other than gallium. Metal ions with applications in nuclear imaging and high affinity for NOTA include copper and indium, in particular the copper isotopes $^{60}$Cu, $^{61}$Cu, $^{62}$Cu, $^{64}$Cu, and $^{67}$Cu or the indium isotope $^{111}$In.

Other radio-labeled alginate conjugates may also be used. For example, the alginate may be conjugated to an iodinated tyramine or tyramine derivative. In some embodiments, the iodinate tyramine or tyramine derivative may have the following formula:

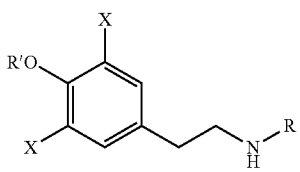

wherein each X is independently hydrogen or iodine and R and R' are each independently hydrogen, alkyl, benzyl or an aromatic group. In some embodiments, the iodine is selected from the isotopes of $^{123}I$, $^{124}I$, $^{125}I$ and $^{131}I$.

$^{68}Ga$ has many potential advantages for clinical PET imaging. Unlike other positron emitters (e.g. $^{18}F$, $^{64}Cu$, and $^{124}I$), $^{68}Ga$ ($T_{1/2}$=68 min, $\beta^+$=89% and EC=11%) can be produced by use of a commercially available $^{68}Ge/^{68}Ga$ generator. Likewise, $^{67}Ga$ has significant advantages for SPECT imaging as it is approved and commercially available for clinical use as the citrate salt. The high specific activity of either isotope allows the production of gallium-labeled NOTA-alginate conjugate with high specific activity suitable for SPECT imaging when used either as a partially cross-linked gallium NOTA alginate conjugate formulation or as a tracer diluted in to a partially cross-linked alginate solution.

An advantage of gallium over other metal ions is that gallium ion forms a very stable complex with derivatives of 1,4,7-triazacyclononane-1,4,7-triacetic acid (NOTA) at room temperature or mammalian body temperature. Although sodium alginate may bind gallium ion, gallium binds to NOTA with higher affinity and the $Ga^{III}$-NOTA complex is stable even in the presence of 100× molar excess of sodium alginate at 37° C. Thus, a NOTA-alginate conjugate can be successfully labeled with stable gallium or radioactive gallium isotopes such as $^{66}Ga$, $^{67}Ga$ and $^{68}Ga$.

The gallium-labeled NOTA-alginate conjugate can be formulated by partial crosslinking with calcium ions for preclinical and clinical use in two different formats.

(1) The gallium-labeled NOTA-alginate conjugate can be formulated as a partially calcium-cross-linked homogeneous solution in which the majority or all alginate molecules are derivatized with NOTA-linker and at least part of all NOTA linker moieties is chelated with radiogallium. Because of the large abundance of NOTA sites in this preparation, the labeling of NOTA with gallium ion can be highly sub-stoichiometric, with gallium bound to only a small fraction of NOTA sites while leaving the majority of all NOTA sites free of gallium ion. To use this material for the imaging of cross-linked alginate deposition, an amount of formulated gallium-labeled NOTA-alginate conjugate similar to that of formulated partially calcium-cross-linked alginate is administered by intracoronary injection. Thus in this format, the partially calcium cross-linked gallium-labeled NOTA-alginate is used instead of and replaces the partially calcium cross-linked alginate.

(2) Alternatively, gallium-labeled NOTA-alginate may be synthesized that contains a high proportion of NOTA sites labeled with gallium ion. This material has sufficiently high specific activity such that such gallium-labeled NOTA alginate conjugate can be used as a tracer by mixing small quantities of the gallium-labeled NOTA alginate conjugate with partially calcium-cross-linked alginate solution for intracoronary injection. When used in this manner, the deposition of gallium-labeled NOTA-alginate conjugate tracks the deposition of partially calcium-cross-linked alginate in the heart tissue by means of its incorporation into the calcium-cross-linked alginate hydrogel.

EXAMPLES

Non-limiting examples of the compounds of the present invention have been synthesized (Examples 1-5), and all intermediates and final products were characterized by $^1$H-NMR, LC-MS and/or elemental analysis). Conditions for labeling NOTA-alginate conjugate with radiogallium are shown in Scheme 6.

Example 1

Synthesis of Tyramine Derivative of NOTA

A tyramine derivative of NOTA was synthesized according to Scheme 1:

Scheme 1: Tyramine Derivative of NOTA

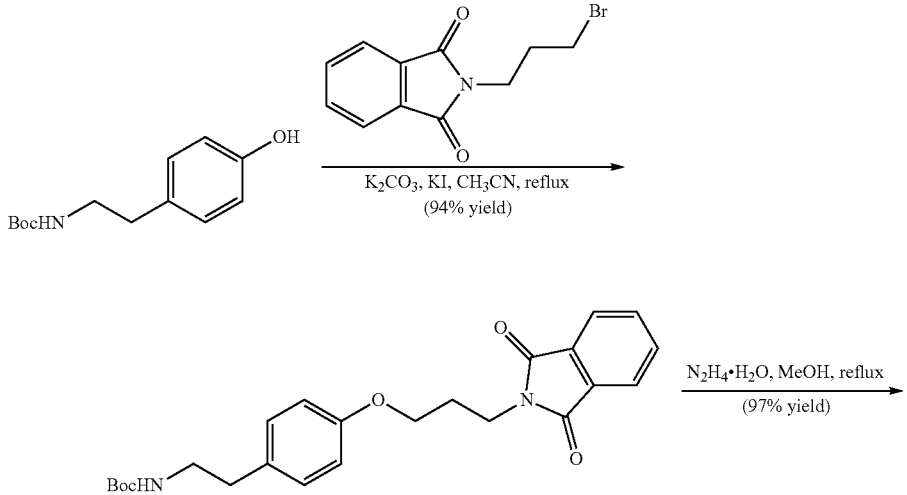

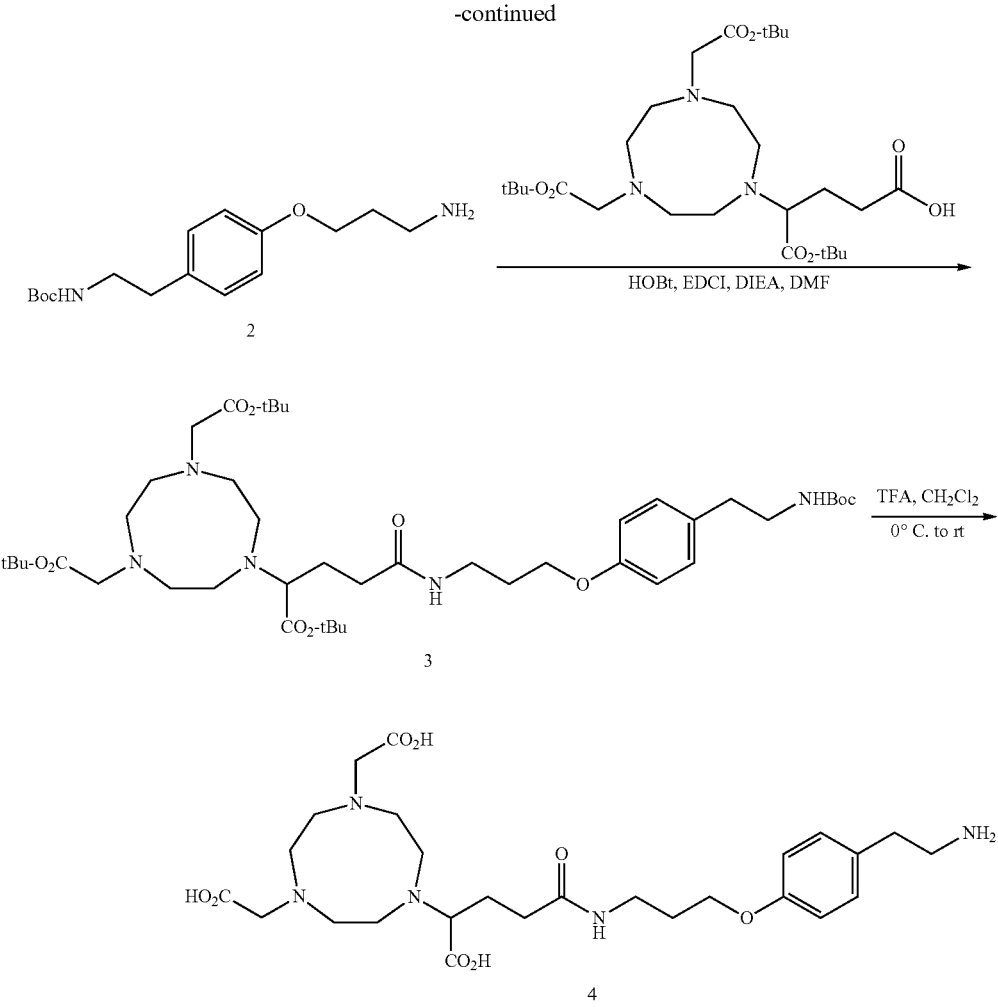

Example 2

Synthesis of NOTA-Alginate Conjugate from Tyramine Derivative of NOTA

The tyramine derivative of NOTA from Example 1 was reacted with sodium alginate in the presence of 4-(4,6-dimethoxy-1,3,5-triazin-2-yl)-4-methylmorpholinium chloride (DMTMM) and water. Scheme 2 shows the formation of an amide bond between the amino group of the tyramine derivative of NOTA and the carboxyl group of the alginate:

Scheme 2: Amide Bond Formation in Aqueous Media by DMTMM

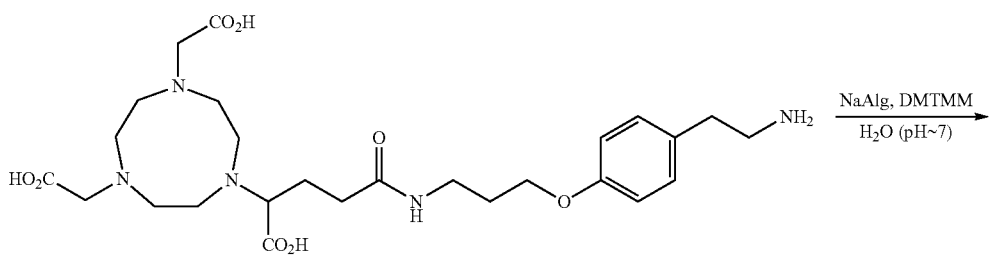

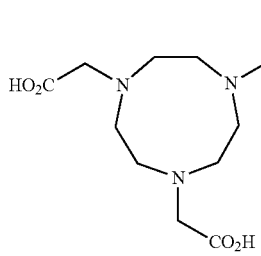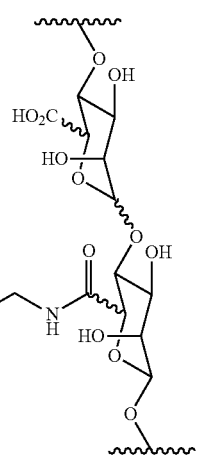

Example 3

Alternative Synthesis of NOTA-Alginate Conjugate from Tyramine Derivative of NOTA An alternative to the reaction shown in Scheme 2 is shown in Scheme 3. The tyramine derivative of NOTA from Example 1 was reacted with alginic acid under the conditions as shown by Scheme 3. Instead of forming an amide bond as in Example 2, reductive amination takes place between the amine in the tyramine derivative of NOTA and the reducing end unit of the alginate.

Scheme 3: Reductive Amination with the Reducing End Unit of Alginate

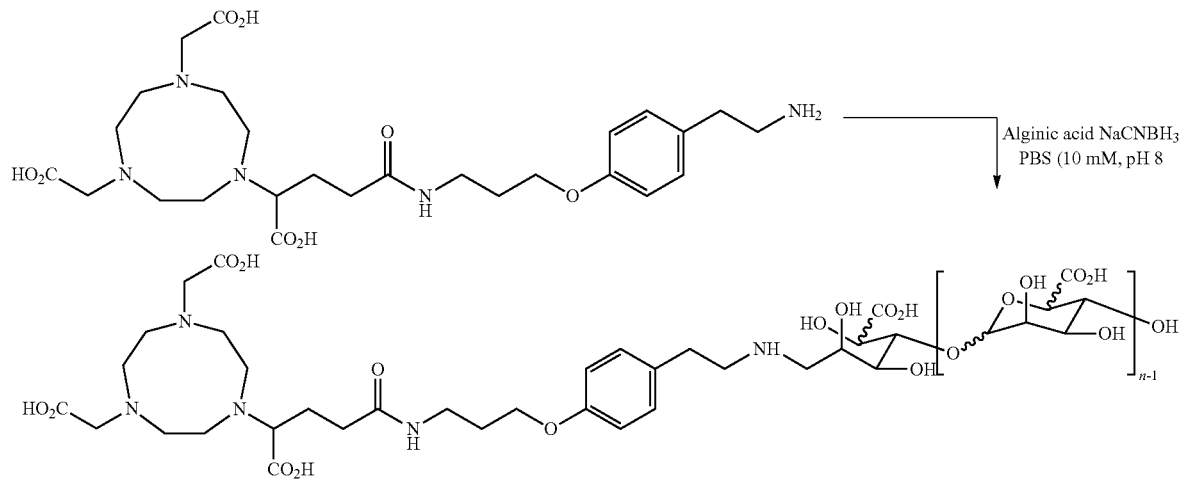

Example 4

Synthesis of N-methylhydroxylamine-Containing NOTA

An N-methylhydroxylamine-containing NOTA linker was synthesized according to Scheme 4:

Scheme 4: Synthesis of N-methylhydroxylamine-Containing NOTA Linker

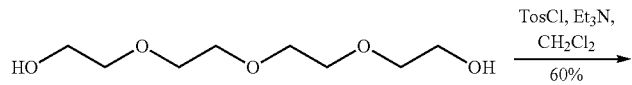

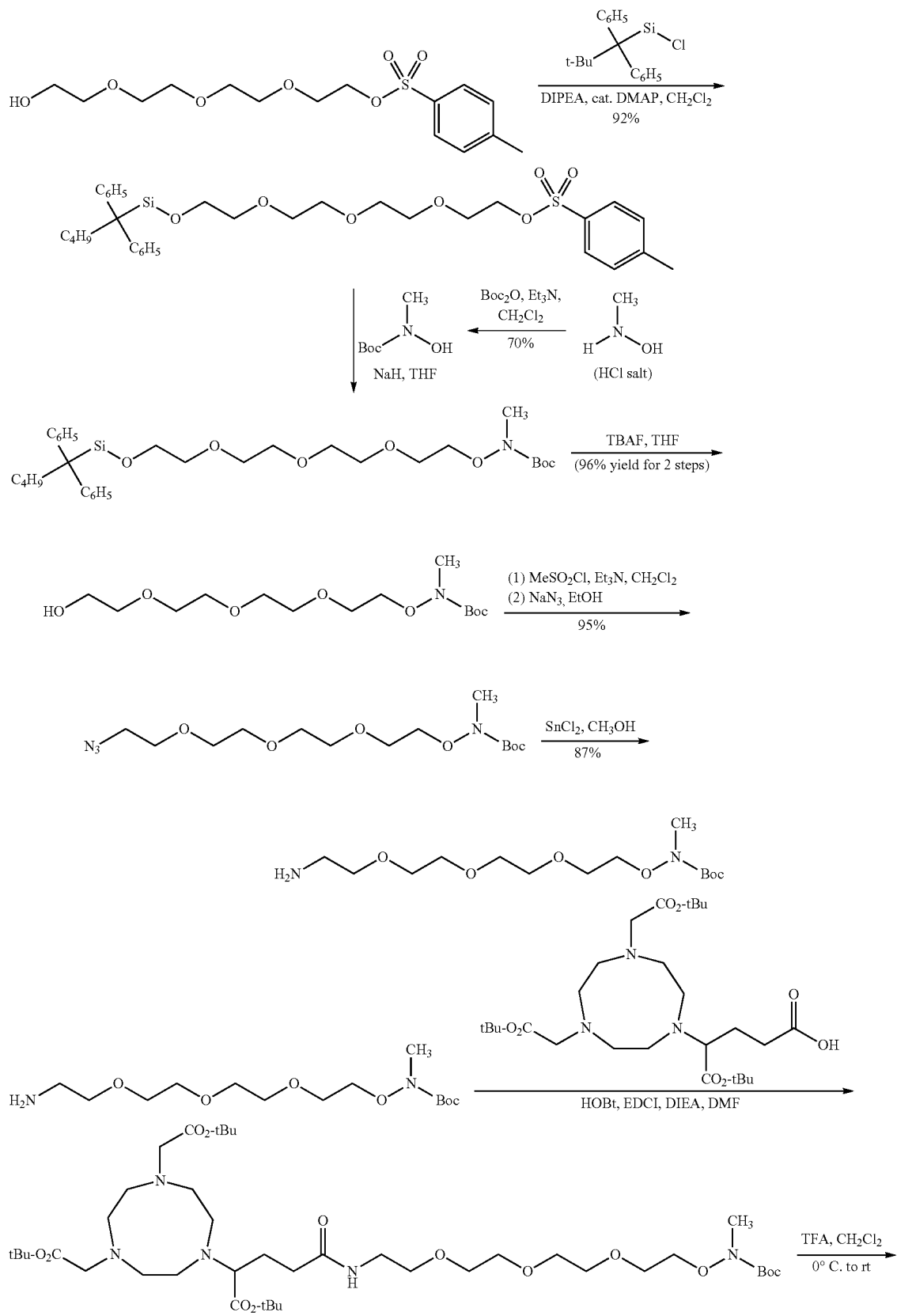

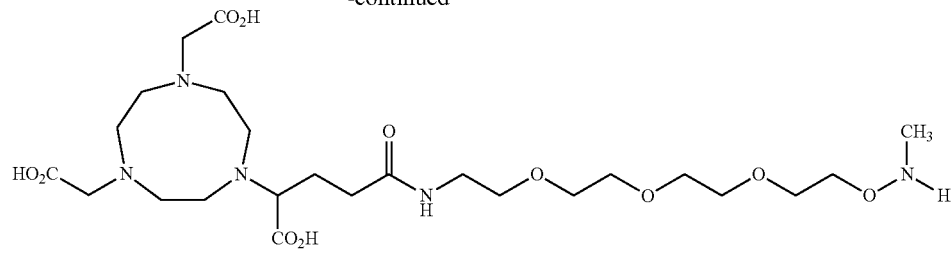

(~60% overall yield for coupling and deprotection steps)

Example 5

Synthesis of NOTA-Alginate Conjugate from N-methylhydroxylamine-Containing NOTA

As shown in Scheme 5, a NOTA-alginate conjugate was produced by directly attaching the N-methylhydroxylamine-containing NOTA linker from Example 4 to the reducing end unit of alginate:

Scheme 5: Direct Attachment to the Reducing End Unit of Alginate

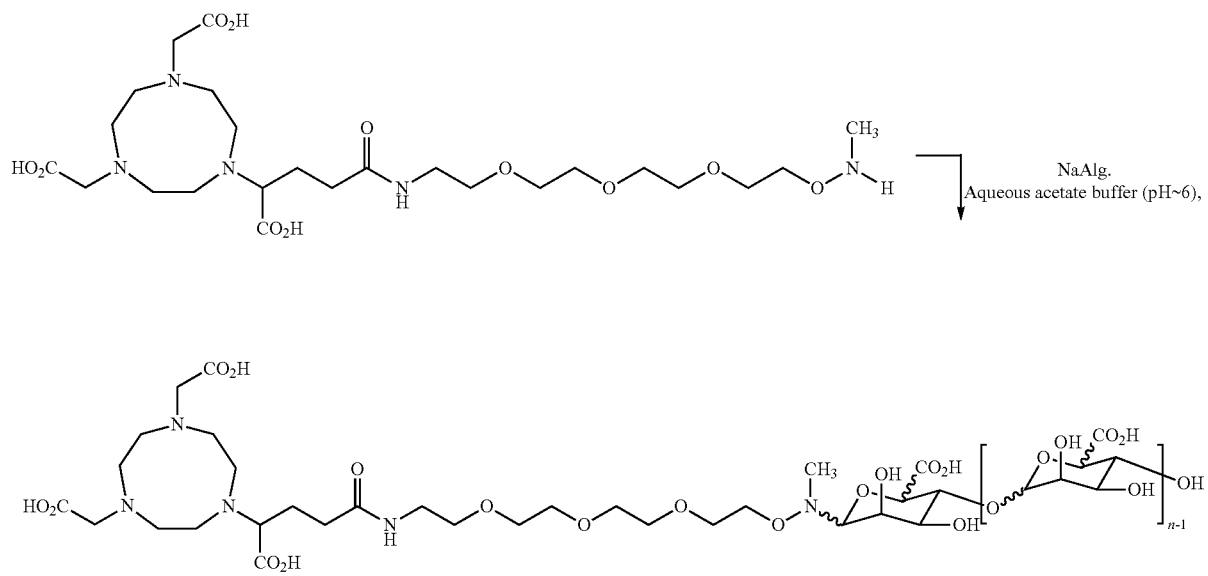

Example 6

Labeling of NOTA-Alginate Conjugate

Scheme 6 shows labeling conditions for NOTA-alginate conjugate: (1) incubation for 15 min at 37° C. of NOTA-alginate conjugate with $^{68}GaCl_3$ eluted from a generator, or $^{67}GaCl_3$ from a cyclotron, (2) rapid separation by gel filtration or molecular weight cutoff filtration of the radio-labeled conjugate from unbound free gallium ion, and (3) either mixing of the gallium-labeled NOTA linker alginate conjugate with partially cross-linked calcium alginate solution for injection or formulation with calcium ions to produce a partially cross-linked gallium-labeled NOTA alginate conjugate.

Scheme 6: Gallium Labeling of NOTA-Alginate Conjugate

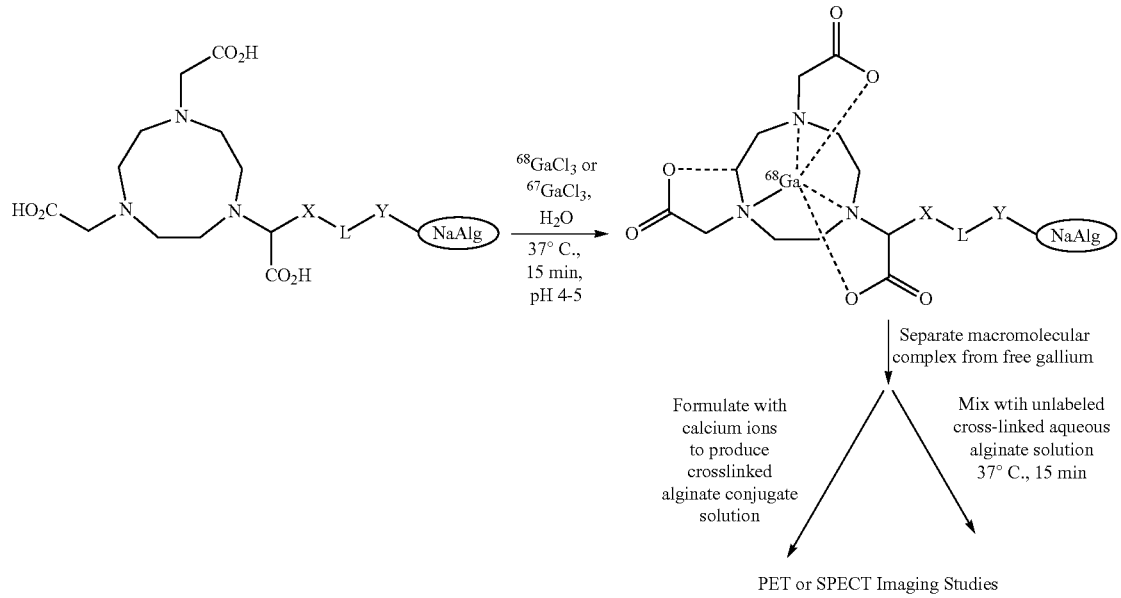

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. An alginate conjugate having the formula:

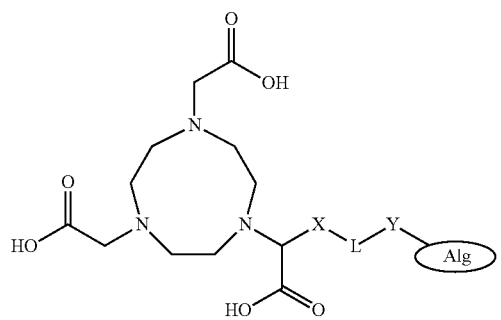

wherein X is —$(CH_2)_mC(O)$—, with m being 1, 2, or 3;

L is a linker selected from the group consisting of:

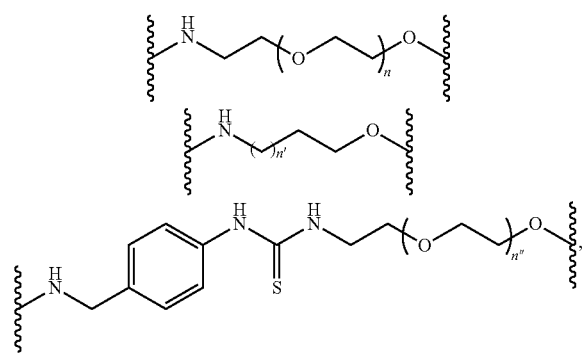

wherein n, n' and n" are each independently a number from 0 to 10;

Alg is alginic acid or an alginate salt; and

Y is a spacer directly attached to the reducing end unit of alginate or the carboxyl groups of the alginate polymer chain via the active nitrogen, and has the following structure:

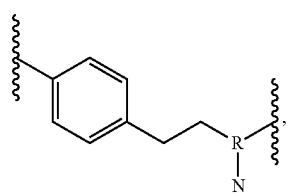

wherein R is selected from the group consisting of hydrogen, alkyl, benzyl or an aromatic group;

or a pharmaceutically acceptable salt or solvate thereof; and, wherein the alginate conjugate comprises a metal ion chelated by the 1,4,7-triazacyclononane-1,4,7-triacetic acid moiety.

2. The alginate conjugate of claim 1, wherein the alginic acid or alginate salt is partially cross-linked.

3. The alginate conjugate of claim 2, wherein the alginic acid or alginate salt is covalently cross-linked by a bifunctional cross-linking agent.

4. The alginate conjugate of claim 2, wherein the alginic acid or alginate salt is cross-linked by divalent or trivalent metal cations.

5. A method of imaging in a mammal comprising:
administering the alginate conjugate of claim 1 to a mammal; and
imaging the temporal and spatial distribution of the alginate conjugate.

6. The method of claim 5, wherein the alginate conjugate is partially cross-linked.

7. The alginate conjugate of claim 6, wherein the alginic acid or alginate salt is covalently cross-linked by a bifunctional cross-linking agent.

8. The alginate conjugate of claim 6, wherein the alginic acid or alginate salt is cross-linked by divalent or trivalent metal cations.

9. A method of imaging alginate deposition in a mammal comprising:
administering a mixture of the alginate conjugate of claim 1 and partially calcium-cross-linked alginate to a mammal; and
imaging the temporal and spatial distribution of the alginate conjugate.

10. The method of claim 9, wherein the alginate conjugate is partially cross-linked.

11. The alginate conjugate of claim 10, wherein the alginic acid or alginate salt is covalently cross-linked by a bifunctional cross-linking agent.

12. The alginate conjugate of claim 10, wherein the alginic acid or alginate salt is cross-linked by divalent or trivalent metal cations.

13. A compound having the formula:

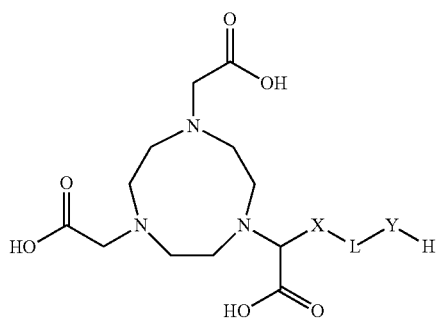

wherein X is $-(CH_2)_mC(O)-$, with m being 1, 2 or 3;
L is a linker selected from the group consisting of:

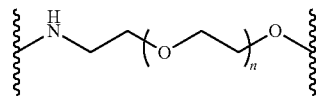

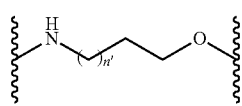

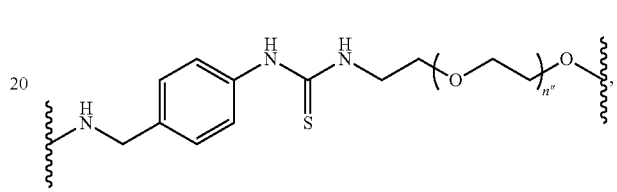

wherein n, n' and n" are each independently a number from 0 to 10;
H is hydrogen; and
Y—H is:

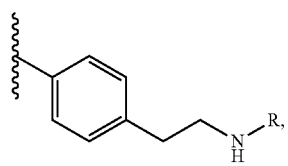

wherein R is selected from the group consisting of hydrogen, alkyl, benzyl or an aromatic group;
or a pharmaceutically acceptable salt or solvate thereof; and
wherein the compound comprises a metal ion chelated by the 1,4,7-triazacyclononane-1,4,7-triacetic acid moiety.

14. The compound of claim 13, wherein the compound further comprises a stable or radioactive metal ion chelated by the 1,4,7-triazacyclononane-1,4,7-triacetic acid moiety.

* * * * *

UNITED STATES PATENT AND TRADEMARK OFFICE
CERTIFICATE OF CORRECTION

PATENT NO. : 9,562,113 B2
APPLICATION NO. : 14/989041
DATED : February 7, 2017
INVENTOR(S) : Fuqiang Ruan et al.

Page 1 of 1

It is certified that error appears in the above-identified patent and that said Letters Patent is hereby corrected as shown below:

In the formula in Claim 1, Column 26, Line 60, should be as shown below:

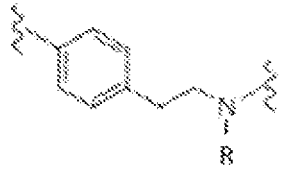

Signed and Sealed this
Thirtieth Day of May, 2017

Michelle K. Lee
*Director of the United States Patent and Trademark Office*